United States Patent [19]

Goring

[11] 4,454,138
[45] Jun. 12, 1984

[54] XANTHINE DERIVATIVES AND THEIR USE IN PHARMACEUTICAL COMPOSITIONS

[75] Inventor: Joachim E. Goring, Gronau, Fed. Rep. of Germany

[73] Assignee: Johann A. Wuelfing, Fed. Rep. of Germany

[21] Appl. No.: 363,125

[22] Filed: Apr. 29, 1982

Related U.S. Application Data

[63] Continuation of Ser. No. 135,285, Mar. 31, 1980, abandoned.

[30] Foreign Application Priority Data

Apr. 5, 1979 [GB] United Kingdom ............... 7912052
Jun. 5, 1979 [GB] United Kingdom ............... 7919505

[51] Int. Cl.$^3$ .................... C07D 239/56; A61K 31/52
[52] U.S. Cl. ..................................... 424/253; 544/267
[58] Field of Search ................. 544/267; 424/253, 251

[56] References Cited

U.S. PATENT DOCUMENTS 2,756,229  7/1956  Stoll et al. ........................... 544/267
3,737,433  6/1973  Mohler et al. ...................... 544/271
4,225,607  9/1980  Goring et al. ...................... 424/253
4,242,345  12/1980 Brenner et al. ..................... 544/267

FOREIGN PATENT DOCUMENTS 2330742  1/1975  Fed. Rep. of Germany .
1167425  11/1953 France .
759174   10/1956 United Kingdom .

OTHER PUBLICATIONS

Armitrage et al., British Jour. Pharm. 17 196–207 (1961).
CA, vol. 57, 5924(h) 1962.
CA, vol. 85, 159334(p) 1976.

Primary Examiner—Nicholas S. Rizzo
Attorney, Agent, or Firm—Jacobs & Jacobs

[57] ABSTRACT

Compounds of the formula (II):

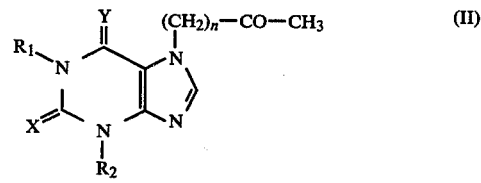

wherein:
X is sulphur and Y is oxygen or sulphur;
$R_1$ is an alkyl group of up to 6 carbon atoms;
$R_2$ is an alkyl group of up to 6 carbon atoms; and
n is 1; or
X is oxygen and Y is sulphur; one of $R_1$ and $R_2$ is an alkyl group of up to 6 carbon atoms and the other is an alkyl group of 2 to 6 carbon atoms; and
n is 1 or 2, having useful pharmacological activity, pro-drugs therefor, a process for their preparation, pharmaceutical compositions containing said compounds or pro-drugs, and intermediates in their preparation of the compounds.

10 Claims, No Drawings

XANTHINE DERIVATIVES AND THEIR USE IN PHARMACEUTICAL COMPOSITIONS

CROSS-REFERENCE

This is a continuation of Ser. No. 135,285 filed Mar. 31, 1980 now abandoned.

British Patent Specification No. 1441562 discloses inter alia that compounds such as those of the formula (I):

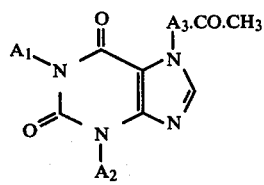

wherein $A_1$ and $A_2$ are alkyl groups and $A_3$ is an alkylene moiety possess blood flow improving properties. A. K. Armitage et al., British J. Pharmacol., (1961), 17, 202 discloses 7-acetylmethyl-1,3-dimethyl-6-thioxanthine as a bronchodilator and coronary dilator.

It has now been found that a class of compounds yet further removed from naturally occuring xanthines effect an improvement in the metabolic status of ischaemic sketal muscle, by increasing oxygen tension and/or contractility in the tissue. The compounds are thus of potential use as agents for the treatment of peripheral vascular diseases such as intermittent claudication.

The present invention provides the structurally distinct compounds of the formula (II):

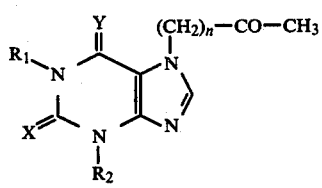

wherein:
X is sulphur and Y is oxygen or sulphur;
$R_1$ is an alkyl group of up to 6 carbon atoms;
$R_2$ is an alkyl group of up to 6 carbon atoms; and n is 1;
or
X is oxygen and Y is sulphur; one of $R_1$ and $R_2$ is an alkyl group of up to 6 carbon atoms and the other is an alkyl group of 2 to 6 carbon atoms; and
n is 1 or 2; or a pro-drug therefor.

When used herein the term "pro-drug" means a compound metabolised in vivo to a compound of the formula (I) or its salt. A pro-drug may be identified by administering the pro-drug to a mammal such as a rat, mouse, monkey or man and identifying the compound of the formula (I) or its salt, in for example blood or urine.

When n is 1 or 2, it is preferably 1. Thus, certain particularly suitable compounds of the formula (II) are those of the formula (III):

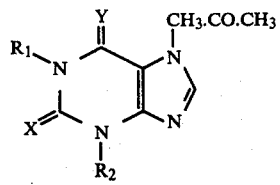

wherein $R_1$, $R_2$, X and Y are as defined in relation to formula (II); or a pro-drug therefor.

Alkyl groups $R_1$ and $R_2$ worthy of mention for the compounds of the formulae (II) and (III) include the methyl ethyl, iso-propyl, n-butyl, iso-butyl, n-pentyl and n-hexyl groups.

Favourably in formulae (II) and (III) $R_1$ and $R_2$ together contain 3–10 carbon atoms and more favourably they together contain 4, 5, 6, 7 or 8 carbon atoms.

Aptly Y in the compounds of the formulae (II) and (III) is an oxygen atom and X is a sulphur atom.

Thus certain favoured compounds of this invention include those of the formula (IV), or a pro-drug therefor:

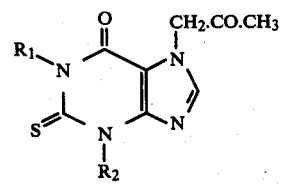

wherein $R_1$ and $R_2$ are as defined in formula (II).

Alkyl groups $R^1$ and $R^2$ worthy of mention and favourable total carbon atom numbers therefor are as to described under formula (III).

A preferred value for $R_1$ in formula (IV) is the n-butyl group. Ethyl is also of interest.

A preferred value for $R_2$ in formula (IV) is the n-butyl group. Ethyl is also of interest.

From the foregoing it will be appreciated that one compound possessing particularly suitable properties is that of the formula

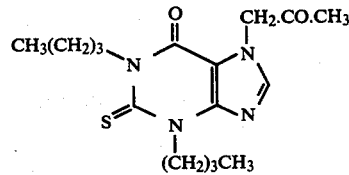

Also aptly Y in the compounds of the formula (II) is a sulphur atom and X is an oxygen atom.

Thus certain other favoured compounds of this invention include those of the formula (V) or a pro-drug therefor

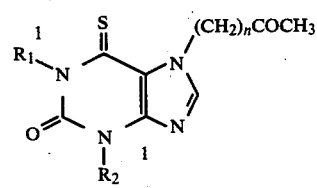

wherein n is as defined in relation to formula (II); and one of $R_1^1$ and $R_2^1$ is an alkyl group of up to 6 carbon atoms and the other is an alkyl group of 2 to 6 carbon atoms.

Suitable groups $R_1^1$ and $R_2^1$ include ethyl, iso-propyl, n-butyl, isobutyl, n-pentyl and n-butyl.

Favourably $R_1^1$ and $R_2^1$ together contain 4–10 carbon atoms, more favourably 4, 5, 6, 7 or 8 carbon atoms.

Preferably $R_1$ is butyl and $R_2$ is ethyl.

Other compounds of this invention are of the formula (VI), or a pro-drug therefor:

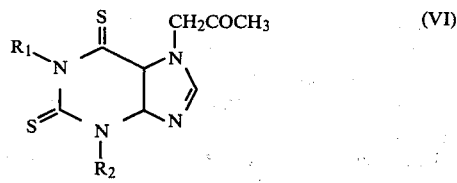

wherein $R_1$ and $R_2$ are as defined in relation to formula (II).

Alkyl groups $R_1$ and $R_2$ are worthy of mention and favourable total carbon atom numbers therefor are as so described under formula (III).

Preferably $R_1$ and $R_2$ are both n-butyl.

Compounds of the formula (II) have useful pharmacological activity, as disclosed hereinbefore, in effecting an improvement in the metabolic status of ischaemic skeletal muscle, by increasing oxygen tension or contractility in the tissue.

Individual compounds of the formula (II) have one or both of these activities. The individual activity profile may be readily ascertained by the two routine pharmacological tests disclosed hereinafter. Nevertheless examples of compounds of interest for each or both activities are given here:

Examples of compounds of the formula (II) which are of particular interest for their activity in increasing ischaemic skeletal muscle contractility are those of the formulae (IV) and (V).

Examples of compounds of the formula (II) which are of particular interest for their activity in increasing oxygen tension in ischaemic skeletal muscle are those of the formula (VI), in particular 1,3-di-n-butyl-7-(2-oxopropyl)-2,6-thioxanthine.

Examples of compounds of the formula (II) which are of particular interest for both of the foregoing activities are those of the formulae (IV) and (V) having the preferred variable values so described under the relevant formula.

As mentioned hereinbefore the compounds of the formula (II), which have either or both of these activities are of potential use for the treatment of peripheral vascular diseases, such as intermittent claudication.

The present invention therefore also provides a pharmaceutical composition which comprises a compound of the formula (II) or a pro-drug therefore and a pharmaceutically acceptable carrier.

The composition of this invention will normally be provided in the form of a discrete unit dose such as a tablet, capsule or defined quantity of the composition in a form suitable for dissolution to provide an injectable solution. Particularly suitable forms of such compositions are those adapted for oral administration such as tablets or capsules.

Unit dose compositions of this invention may contain 1 to 500 mgs of active agent. Compounds of this invention wherein the 7-position side chain is other than 2-oxopropyl or a group convertible thereto will normally be present in such compositions in a dose from 100 to 500 mgs, for example 200 to 400 mgs. Compounds of this invention wherein the 7-position side chain is 2-oxopropyl or a group convertible thereto will normally be present in such compositions in a dose of from 1 to 100 mgs, more usually 2.5 to 50 mgs for example 5 to 25 mgs. The unit dose composition will normally be taken from 1 to 4 times daily so that the normal dose for a 70 kg adult human will be from about 100 to 2000 mgs for a composition containing a compound in which the 7-position substituent is other than 2-oxopropyl or a group convertable thereto and from about 4 to 100 mgs for a composition containing a compound in which the 7-position substituent is a 2-oxopropyl group or a group convertable thereto.

The compositions of this invention may be formulated in conventional manner. Thus oral dosage units may contain such conventional agents as fillers (diluents), lubricants, binders, disintegrants, colourants, flavourings, surface active agents, preservatives, buffering agents, and the like. Suitable fillers for use include cellulose, mannitol, lactose and other similar agents. Suitable disintegrants include starch, polyvinylpolypyrrolidone and starch derivatives such as sodium starch glycollate and the like. Suitable lubricants include stearic acid, magnesium stearate, magnesium lauryl sulphate and the like. Injectable compositions may consist essentially of a sterile, pyrogen free compound of this invention sealed into a vial optionally together with suspending and preserving agents. Such compositions may be made up for administration with sterile water or saline.

The compositons may be prepared by conventional methods of blending, filling, tabletting or the like.

The present invention also provides a process for the preparation of the compounds of this invention which process comprises the reaction of a salt of a compound of the formula (VII):

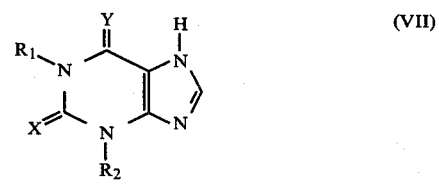

wherein $R_1$, $R_2$, X and Y are as defined in relation to formula (II) with a compound of the formula (VIII):

$$Cl-(CH_2)_n-CO-CH_3 \qquad (VIII)$$

wherein n and m are as defined in relation to formula (II) or a chemical equivalent thereof.

Suitable chemical equivalents of the chloro-compound of the formula (VIII) include the corresponding bromo- and iodo-compounds and analogous active esters such as mesylates or tosylates.

The salt of the compound of the formula (VII) will normally be an alkali metal salt such as the sodium or potassium salt and may be performed or generated in situ by the presence of a base such as an hydroxide or ethanolate.

Suitable solvents for use in such processes include lower alkanols such as methanol, ethanol or the like.

The reaction is generally carried out at an ambient or elevated temperature, for example from 20° to 80° C. It is often convenient to carry out the reaction in a solvent under reflux.

When the desired compound has been produced it may be recovered by distilling off the solvent, by precipitation with a miscible non-solvent or the like.

Purification of the compound of this invention may be carried out by conventional methods such as crystallisation, recrystallisation and chromatography.

Compounds of the formula (II) wherein n is 2 may be prepared by the reaction of a compound of the formula (VII) with methyl vinyl ketone or 2-chlorobutan-3-one. This reaction may be carried out under conditions as described herein for reaction with a compound of the formula (VIII).

Certain compounds of the formula (VII) are novel and form part of this invention. Thus the present invention provides the compound of the formula (VII) as hereinbefore described wherein $R_1$ and $R_2$ are each n-butyl groups, X is sulphur and O is oxygen or sulphur and salts thereof.

Compounds of the formula (VII) wherein Y is a sulphur atom and X is an oxygen atom may be prepared by the process of K. R. H. Wooldrige and R. Slack, J. Chem. Soc., 1962, 1863–68.

The compounds of the formula (VII) wherein X is a sulphur atom and Y is an oxygen atom may be prepared by the reaction of a compound of the formula (IX):

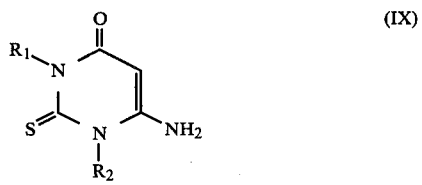

wherein $R_1$ and $R_2$ are as defined in relation to formula (II) with sodium carbonate, formamide, formic acid and sodium dithionite. This reaction is generally begun at a depressed temperature such as 3°–5° C. and gradually warmed until completion occurs at an elevated temperature such as 160°–190° C.

The compounds of formula (IX) may be prepared according to the procedures of Bredeneck et al., Chem. Ber., 88, 1306–1312 (1955). Their conversion into compounds of the formula (VIII) as described above may be viewed in the light of Papesch et al., U.S. Pat. No. 2,615,020.

Compounds of the formula (VII) wherein X and Y are both sulphur atoms may be prepared by the reaction of $P_4S_{10}$ and a compound of the formula (VIII) wherein one of X and Y is a sulphur atom and the other is an oxygen atom or both of X and Y are oxygen atoms; see for example U.S. Pat. No. 3,135,753, Chem. Zentralblatt 37-2695 (1966), Chem. Zentralblatt 27-1557 (1966) and Chem. Zentralblatt 40-0983 (1968).

The invention also provides a method for the treatment or prophylaxis of peripheral vascular disease, which method comprises the administration to the sufferer of a therapeutically effective amount of a compound of the formula (II) or a pro-drug therefor.

The following Examples illustrate the invention.

EXAMPLE 1

1-n-Butyl-3-ethyl-7-(2-oxopropyl)-6-thioxanthine(1)

1-n-Butyl-3-ethyl-6-thioxanthine (4 g) was dissolved in dimethyl formamide (30 ml) and a small amount of potassium carbonate was added. To this mixture, 1-bromopropan-2-one (2,7 g) was added dropwise at room temperature, with stirring. The reaction was heated at about 50° C. for two hours. The reaction mixture was then extracted with chloroform several times, the chloroform phase washed with 1N KOH and water, dried with sodium sulphate, filtered and the chloroform removed in vacuo to yield a red/brown oil which, on crystallisation in a mixture of ethylacetate/petroleum, gave 1-n-butyl-3-ethyl-7-(2-oxopropyl)-6-thioxanthine as a white powder.

Melting point: 173°–174° C.
Yield: 1 g.

| | Elemental Analysis | |
|---|---|---|
| | Calculated | Found |
| C | 54,55 | 55,14 |
| H | 6,49 | 6,34 |
| N | 18,19 | 17,89 |
| O | 10,39 | 10,60 |
| S | 10,39 | 10,01 |

EXAMPLE 2

1,3-Di-n-butyl-7-(3-oxobutyl)-6-thioxanthine (2)

1,3-di-n-butyl-6-thioxanthine (8,3 g), methylvinylketone (2,9 ml) and triethylamine (1 ml) were dissolved in ethanol (10 ml) and the mixture was slowly heated with stirring at 40°–50° C. for one hour. After cooling of the clear solution, the 1,3-di-n-butyl-7-(3-oxobutyl)-6-thioxanthine precipitated in the form of yellow needles.

Melting point: 118–119° C.
Yield: 8,5 g

| | Elemental Analysis | |
|---|---|---|
| | Calculated | Found |
| C | 58,29 | 58,28 |
| H | 7.43 | 7.40 |
| N | 16,00 | 16,12 |
| O | 9,14 | 9,27 |
| S | 9,14 | 8,90 |

The structure was confirmed by NMR spectroscopy.

Using an analogous process the following were prepared: 1-n-butyl-3-ethyl-7-(3-oxobutyl)-6-thioxanthine (3), m.pt. 127° C., was prepared in 75% yield. The crystallisation solvent was ethanol.

| | Elemental Analysis | | | | |
|---|---|---|---|---|---|
| | C % | H % | N % | O % | S % |
| Calculated | 55,90 | 6,83 | 17,39 | 9,94 | 9,94 |
| Found | 56,08 | 6,91 | 16,91 | 10,23 | 9,87 |
| | 55,95 | 6,92 | 17,03 | 10,35 | 9,85 |

1,3-dimethyl-7-(3-oxobutyl)-6-thioxanthine (4), m.pt. 164° C., was prepared in 77% yield. The crystallisation solvent was ethyl acetate/methanol.

| | Elemental Analysis | | | | |
|---|---|---|---|---|---|
| | C % | H % | N % | O % | S % |
| Calculated | 46,62 | 5,26 | 21,05 | 12,03 | 12,03 |
| Found | 49,54 | 5,36 | 21,29 | 11,96 | 11,93 |
| | 49,46 | 5,37 | 21,26 | 11,96 | 11,84 |

EXAMPLE 3

1,3-Di-n-butyl-2-thioxanthine (5)

Sodium carbonate (8 g) was dissolved in formamide (200 ml) and 1,3-di-n-butyl-2-thio-4-aminouracil (32 g) was added at a temperature of 3° C. with stirring. The mixture was cooled over a period of 1 hour and at a temperature of 3°-5° C. Formic acid (16 ml) was added dropwise. The reaction mixture was allowed to stand overnight in a refrigerator. The mixture was then heated to 100° C. and then sodium dithionite (5 g) was added at this temperature. To complete the reaction, the mixture was heated to 190° C. for 1 hour. After cooling to room temperature with stirring, the oil solidified with crystallisation. The crude product was filtered with suction. To remove coloured by-products, the crude product was dissolved in dilute sodium hydroxide, the solution treated with charcoal and precipitated with acetic acid and the compound was recrystallised from methanol/water to give 1,3-di-n-butyl-2-thioxanthine as white powder.

Melting point: 137° C.
Yield: 27,2 g

| | Elemental Analysis | |
|---|---|---|
| | Calculated | Found |
| C | 55,69 | 55,76 |
| H | 7,19 | 7,16 |
| N | 19,98 | 19,90 |
| O | 5,77 | 5,82 |
| S | 11,43 | 11,44 |

EXAMPLE 4

1,3-Di-n-butyl-7-(2-oxopropyl)-2-thioxanthine (6)

1,3-Di-n-butyl-2-thioxanthine (12,6 g) was treated with sodium (1,05 g) in absolute ethanol (45 ml) to give the 1-3-di-n-butyl-2-thioxanthine sodium salt by heating under reflux for one hour. 1-Bromo-propan-n-2-one (ml) was then added dropwise and the reaction mixture was heated under reflux for a further hour. After cooling to room temperature, the precipitated sodium bromide was filtered off and the solution was evaporated to dryness. The residue was dissolved in chloroform and treated with dilute NaOH to remove unreacted starting material. The chloroform phase was washed with water, dried, filtered and evaporated in vacuo to dryness. This residue was dissolved in methanol and treated with charcoal to remove the colour of the solution. After standing, the 1,3-di-n-butyl-7-(2-oxopropyl)-2-thioxanthine precipitated as a white powder.

Melting point: 131°-132° C.
Yield: 3,5 g

| | Elemental Analysis | |
|---|---|---|
| | Calculated | Found |
| C | 57,12 | 57,16 |
| | Elemental Analysis | |
| | Calculated | Found |
| H | 7,19 | 7,24 |
| N | 16,65 | 16,80 |
| O | 9,51 | 9,40 |
| S | 9,53 | 9,56 |

EXAMPLE 5

1,3-Di-n-butyl-7-(2-oxopropyl)-6-thioxanthine (7)

1,3-Di-n-butyl-6-thioxanthine (5,6 g) was treated with sodium (0,46 g) in absolute ethanol (20 ml) to give the 1,3-di-n-butyl-6-thioxanthine sodium salt by heating under reflux for one hour. 1-chloropropan-2-one (2,31 g) dissolved in ethanol (20 ml) was added dropwise and the reaction mixture heated under reflux for a further 5 hours. The reaction was then complete (as judged by TLC). After standing overnight, the precipitated sodium chloride was filtered off under suction. The dark filtrate was extracted with chloroform. The chloroform phase was washed three times with 1N NaOH, washed with water, dried with sodium sulphate, filtered and the chloroform was removed in vacuo to yield a dark brown residue. On crystallisation from ethanol the residue gave 1,3-di-n-butyl-7-(2-oxo-propyl)-6-thioxanthine as a white powder.

Melting point: 152° C.
Yield: 0,6 g

| | Elemental analysis: | |
|---|---|---|
| | Calculated | Found |
| C | 57,11 | 57,29 |
| H | 7,19 | 7,02 |
| N | 16,65 | 16,73 |
| O | 9,50 | 9,61 |
| S | 9,55 | 9,50 |

The structure was confirmed by NMR spectroscopy. Using an analogous process the following two compounds were prepared:

1,3-Di-n-butyl-7-(2-oxopropyl)-2,6-di-thioxanthine (8)

Melting point: 173° C.
Yield: 1,2 g
crystallisation solvent: ethanol

| | Elemental analysis: | |
|---|---|---|
| | Calculated | Found |
| C | 54,52 | 54,64 |
| H | 6,86 | 6,81 |
| N | 15,89 | 15,93 |
| O | 4,54 | 4,74 |
| S | 18,19 | 17,87 |

The structure was confirmed by NMR spectroscopy.

1,3-Di-ethyl-7-(2-oxopropyl)-2-thioxanthine (9)

Melting point: 202° C.
Yield: 7,9 g ≙ 41,9% of the theory
crystallisation solvent: ethanol

| | Elemental analysis: | |
|---|---|---|
| | Calculated | Found |
| C | 51,41 | 51,18 |

|   | Elemental analysis: | |
|---|---|---|
|   | Calculated | Found |
| H | 5,75 | 6,02 |
| N | 19,98 | 19,95 |
| O | 11,41 | 11,44 |
| S | 11,44 | 11,36 |

The structure was confirmed by NMR spectroscopy.

EXAMPLE 12

Composition 1,3-Di-n-butyl-7-(2-oxopropyl)-2-thioxanthine, magnesium stearate and microcrystalline cellulose may be blended together and passed through a 40 mesh sieve (UK). The resulting mixture may be tabletted on a conventional rotary machine to produce a batch of 5000 tablets of the following composition:

1,3-Di-n-butyl-7-(2-oxopropyl)-2-thioxanthine: 10 mg
magnesium stearate: 0.2 mg
microcrystalline cellulose: 189.8 mg

Pharmacology

Methodology

Cats of either sex were anaesthetized by i.p. injection of urethane/chloralose (120/60 mg/kg). The intraduodenal (i.d.) administration of compounds was conducted by means of a plastic catheter which was inserted into the duodenum following midline incision at the abdominal cavity.

(i) pO2-measurements

Measurement of muscle surface pO$_2$. The skin above the measuring site (3–4 mm in diameter) was removed and one multiwire-surface electrode (Eschweiler, Kiel) was placed on the gastrocnemius muscle of each hindlimb. The femoral artery in one hindlimb was ligated in order to induce ischaemia. Muscle temperature was controlled by means of a thermocouple (Ellab, Copenhagen). The electrode current was measured every 6 to 8 s and collected for periods of 4 min (Hewlett-Packard programmable data logger system 3051 A). After each period, mean value and standard deviation was calculated.

(ii) Skeletal muscle contractility

After dissection of the skin of the calf muscles, the sciatic nerve was cut about 3 cm proximal to the knee. The tendon of the calf muscles was cut and connected with an isometric force transducer (SWEMA, SG 3). In order to maintain constant differences and a resting tension of 100 p in cats and 25 p in rats, the hindlimb was fixed at the tibia by means of a clamp. Direct stimulation of the muscles consisted of square wave pulses of 4 msec duration at a frequency of 2 Hz and at a voltage 50 V in cats. In order to keep the muscles wet and at a normal temperature, the muscles were continously superfused with 0.9% w/v NaCl solution (38° C.). Femoral blood flow was restricted by a graded occlusion of the artery leading to a reduction of contractility by ca. 30%. After having reached a constant level of the contraction force, the appropriate vehicle (NaCl or Methocel) was injected, followed by the test substance.

Results

| | | | (i) pO2-measurements | | | | | |
|---|---|---|---|---|---|---|---|---|
| | dosage (mg/ kg) | | hypoxic tissue | | | normoxic tissue | | |
| Compound | i.d.* | n | $C_s$ | $\Delta pO_2$ | E | $C_s$ | $\Delta pO_2$ | E |
| 1 | 12.5 | 2 | 1 | 1.4 | 1.4 | 1 | 12.9 | 12.9 |
| 3 | 12.5 | 3 | 0.67 | 3.8 | 2.7 | 1 | 7.0 | 7.0 |
|   | 32.0 | 3 | 0.67 | 4.5 | 3.0 | 1 | 2.0 | 2.0 |
| 6 | 0.1 | 4 | 1 | 6.2 | 6.2 | 0.67 | 8.4 | 5.7 |
|   | 0.3 | 4 | 1 | 5.3 | 5.3 | 1 | 5.7 | 5.7 |
| 8 | 2.0 | 4 | 0.75 | 6.6 | 5.0 | 0.5 | 9.9 | 4.9 |

| (ii) skeletal muscle contractility | | | | | | |
|---|---|---|---|---|---|---|
| Compound | dosage (mg/ kg) i.d.* | n | average increase (%)° | Compound | dosage (mg/kg) i.d.* | n | average increase (%)° |
| 1 | 2.0 | 2 | +22.2 | 6 | 0.3 | 2 | +5.3 |
|   | 5.0 | 2 | +12.1 |   | 0.8 | 3 | +7.5 |
|   |   |   |   |   | 2.0 | 4 | +10.3 |
|   |   |   |   |   | 5.0 | 3 | +17.1 |
| 3 | 12.5 | 2 | +10.4 | 9 | 32.0 | 2 | +9.4 |
| 4 | 12.5 | 1 | +7.1 |   |   |   |   |
|   | 32.0 | 3 | +21.1 |   |   |   |   | n = number of animals
$C_s$ = significance coefficient = number of measuring sites with significant pO$_2$ increase per total number of measuring sites $\overline{\Delta pO_2}$ = mean pO$_2$ increase in experiments with significant pO$_2$ increase (Torr)
E = efficiency - index = $C_s \times \overline{\Delta pO_2}$ (Torr)
Control values: E between 0 and 1.4 Torr
*i.d. = intraduodenal application of a suspension in Methocel (methyl cellulose)
(%)° of initial values

Toxicity

No toxic effects were observed at the test dosages.

I claim:
1. 1,3-Di-n-butyl-7-(2-oxopropyl)-2-thioxanthine.
2. The compound of claim 1 in solid form.
3. The compound of claim 1 in essentially pure form.
4. 1,3-Diethyl-7-(2-oxopropyl)-2-thioxanthine.
5. The compound of claim 4 in solid form.
6. The compound of claim 4 in essentially pure form.
7. A pharmaceutical composition for treatment of peripheral vascular disease which comprises an effective amount of a compound according to claim 1 or 4 together with a pharmaceutically acceptable carrier.
8. A method of treatment of an animal suffering from a pheripheral vascular disease, which comprises administering to the animal an effective amount of a compound of the formula (IV):

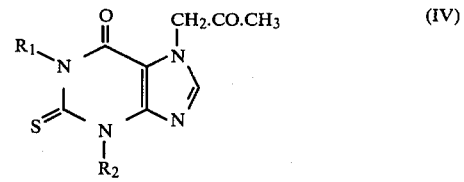

wherein R$_1$ and R$_2$ are each alkyl of 1 to 6 carbon atoms or a pro-drug therefor.

9. The method according to claim 8, wherein said compound is 1,3-di-n-butyl-7-(2-oxopropyl)-2-thioxanthine.

10. The method according to claim 8, wherein said compound is 1,3-diethyl-7-(2-oxopropyl)-2-thioxanthine.

* * * * *